United States Patent [19]

Kimura et al.

[11] Patent Number: 5,747,989
[45] Date of Patent: May 5, 1998

[54] APPARATUS FOR NON-DESTRUCTIVELY DETECTING A NUGGET FOR SPOT WELDING

[75] Inventors: Takashi Kimura, Nagoya; Kaneyasu Arakawa, Ichinomiya, both of Japan

[73] Assignee: Kyokutoh Co., Ltd., Aichi, Japan

[21] Appl. No.: 551,776

[22] Filed: Nov. 7, 1995

[30] Foreign Application Priority Data

Nov. 11, 1994 [JP] Japan ................. 6-015069 U

[51] Int. Cl.⁶ ............................ G01N 27/72; G01R 33/12
[52] U.S. Cl. ........................ 324/235; 324/240; 324/242
[58] Field of Search ............................ 324/233, 234, 324/235, 238–243, 262

[56] References Cited

U.S. PATENT DOCUMENTS

| | | | |
|---|---|---|---|
| 3,315,155 | 4/1967 | Colani | 324/239 |
| 3,359,495 | 12/1967 | McMaster et al. | 324/235 |
| 3,526,829 | 9/1970 | Noble | 324/238 |
| 3,710,236 | 1/1973 | Halsey et al. | 324/235 |
| 4,207,519 | 6/1980 | Zatsepin et al. | 324/235 |
| 4,287,474 | 9/1981 | Fastritsky et al. | 324/233 |
| 5,059,902 | 10/1991 | Linder | 324/239 |
| 5,086,274 | 2/1992 | Gobin et al. | 324/242 X |
| 5,134,368 | 7/1992 | Otaka et al. | 324/262 |
| 5,461,313 | 10/1995 | Bohon et al. | 324/240 |

*Primary Examiner*—Gerard R. Strecker
*Attorney, Agent, or Firm*—Koda and Androlia

[57] ABSTRACT

An apparatus for detecting a nugget for spot welding utilizing the magnetic after-effect which is generated when a variation in the magnetic field is applied to a nugget. The apparatus includes a driving coil, which applies a magnetic field variation to a spot-welded nugget, and a magnetism sensing element, which detects variations in magnetic flux density arising in the vicinity of the nugget as a result of the magnetic field variation. The magnetism sensing elements may be installed in an array form so as to face the nugget and the area around the nugget.

2 Claims, 3 Drawing Sheets

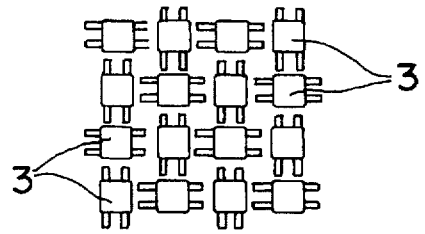
F I G. 5
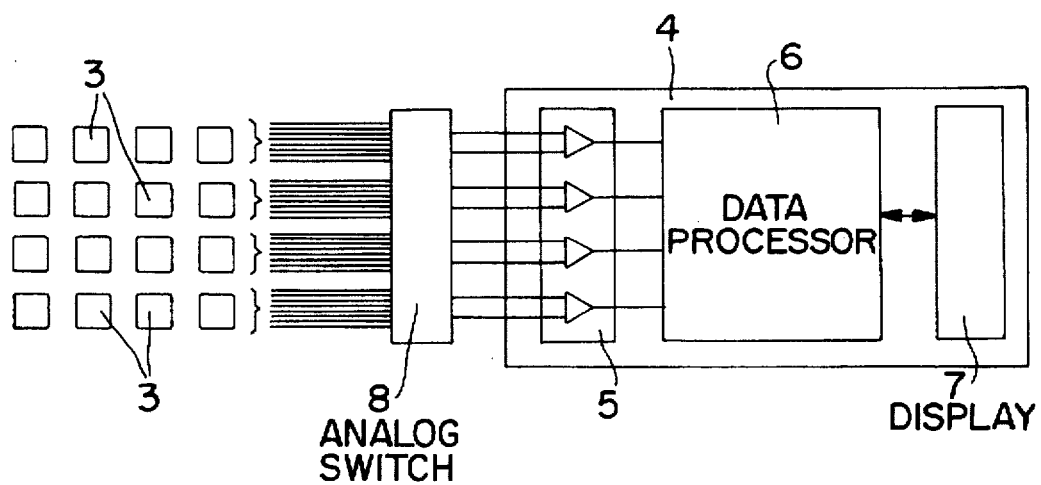
F I G. 6

APPARATUS FOR NON-DESTRUCTIVELY DETECTING A NUGGET FOR SPOT WELDING

BACKGROUND OF THE INVENTION

1. Field of the Invention

The present invention relates to an apparatus for detecting the conditions of welding of nuggets (welded areas) in spot welding off-line and in a non-destructive manner.

2. Prior Art

In the past, several methods for detecting nuggets in spot welding have been known such as a method in which the nugget diameter is estimated from the Joule heat during welding, a method in which the conditions of welding of the nugget are estimated from changes in the inductance of a coil through which a high-frequency current is flowing, and a method called a driver checking method.

The driver checking method is a so-called destructive test method in which the diameter of the nugget is measured by stripping off a welded portion. Accordingly, sample testing or selective testing is necessary, and therefore, the detection of all the welded nuggets cannot be made. On the other hand, the method which utilizes Joule heat is limited to in-line testing (which is a testing performed with the nuggets kept on a manufacturing line) and is unable to detect internal defects of the nugget, especially delamination or cracking, etc. which occurs immediately after the welding. Moreover, in the case of method in which the welding conditions are estimated from changes in inductance, the positional relationship between the nugget and the sensors is extremely delicate, and accurate values cannot be obtained unless such a position relationship is always kept exactly the same. Even for the same workpiece, the measured value will change if the sensors are inclined or moved away from the workpiece. Furthermore, this method is unable to ascertain whether the shape of the nugget is acceptable or not.

SUMMARY OF THE INVENTION

The present invention is created so as to eliminate the problems encountered in conventional methods used for the detection of nuggets in spot welding, and the object of the present invention is to provide a convenient apparatus for detecting spot welded nuggets which can easily and reliably detect the shape and welding conditions of all spot welded nuggets off-line (or removing the nuggets out of a manufacturing line) without destroying the nuggets.

The constitution of the present invention which is used to accomplish the object may be described as follows using drawings which correspond to an embodiment of the present invention, and more specifically, the basic principle of the present invention is that the welding conditions of a spot welded nugget A can be measured utilizing the magnetic after-effect that is generated when a magnetic field variation is applied to the nugget A; and first of all, the apparatus of the present invention is characterized in that the apparatus includes a driving coil 1, which applies a magnetic field variation to a spot welded nugget A, and a magnetism sensing element 3, which detects variations in magnetic flux density arising in the vicinity of the nugget A caused by the magnetic field variation; and secondly, the apparatus of the present invention is characterized in that magnetism sensing elements 3 are installed in an array so as to face the nugget A and the area around the nugget A.

With the means described above, when a magnetic field variation is applied to a spot welded nugget A by actuating the driving coil 1, a magnetic after-effect is generated by the peculiar nature of each magnetic material involved, and in the nugget A, martensite is formed as a result of rapid cooling which occurs after the spot welding so that a difference is generated between the magnetic after-effect generated in the nugget A and the magnetic after-effect generated in the areas outside the nugget A.

With the use of the magnetism sensing element 3, the variations in magnetic flux density that constitutes the magnetic after-effect generated in the vicinity of the nugget A are detected, and the signal thus obtained is data-processed, thus measuring the welding conditions of the nugget A.

If magnetism sensing elements 3 are provided in an array so as to face a nugget A and the area surrounding the nugget A, it is possible to obtain magnetic after-effect data of a broader area which includes the nugget A and its surroundings, thus allowing much more definite measurement of the welding conditions and shape of the nugget A to be accomplished.

BRIEF DESCRIPTION OF THE DRAWING

FIG. 5 is a plan view which shows an example of the installation of magnetism sensing elements in an array.

FIG. 6 is a schematic diagram illustrates a case in which magnetism sensing elements are installed in an array.

DESCRIPTION OF THE PREFERRED EMBODIMENTS

Figure 1:
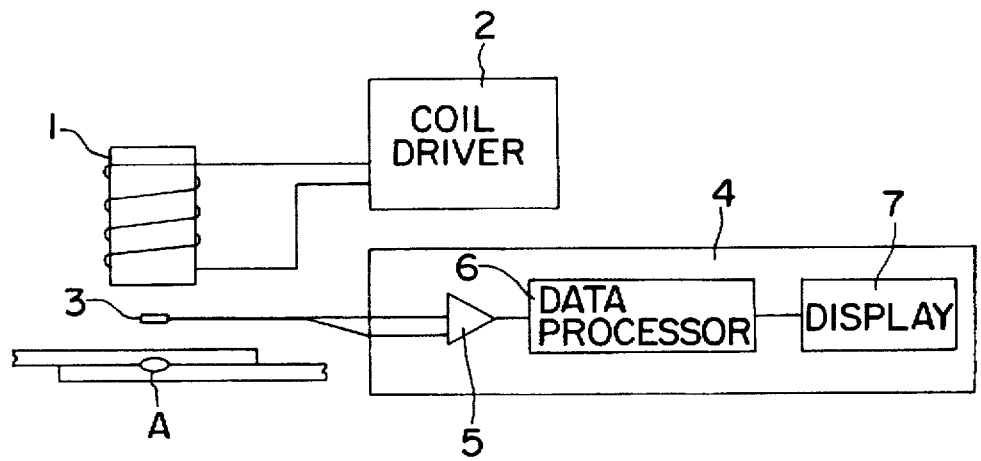
FIG. 1 is an overall schematic diagram.

Below, the present invention is described in terms of an embodiment which is illustrated in the accompanying drawings. FIG. 1 is a schematic diagram of the apparatus of the present invention. In this figure, 1 indicates a driving coil which applies a perpendicular magnetic field to the nugget A that is spot welded and to be measured. A driving coil driver 2 which is electrically connected to the driving coil 1 performs positive and negative pulse driving as shown as an example in FIG. 2. Thus, the driving coil 1 applies a magnetic variation to the nugget A.

3 indicates a magnetism sensing element such as a Hall element, etc., which detects variations in magnetic flux density in the vicinity of the nugget A that are generated by the magnetic field variations caused by the driving coil 1. The magnetism sensing element 3 is fastened in place and supported by being soldered to an appropriate Hall element substrate. The Hall element substrate used in this case is a multi layer substrate, and it is preferable that the + side output pad and the − side output pad be set in identical positions as far as is possible. With this structure, effects on the wiring patterns caused by abrupt variations in the magnetic field can be cancelled out.

4 indicates a control section which measures and analyzes physical properties of the nugget A based upon the detection signals from the magnetism sensing element 3. The control section 4 includes a sensor circuit part 5 which amplifies the detection signals from the magnetism sensing element 3, a data processing part 6 which subjects the signals amplified by the sensor circuit part 5 to A/D conversion and data processing, and a display part 7 which is used for displaying and setting the processed data.

Figure 2:
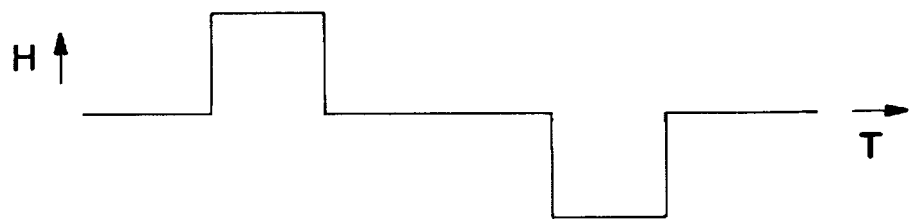
FIG. 2 shows the pulse driving waveform of the driving coil.

In the above structure, the magnetism sensing element 3 is set so as to face the position of the nugget A which is spot welded and to be measured, and a pulse driving waveform as shown as an example in FIG. 2 is applied to the driving coil 1 using the driving coil driver 2 This pulse driving waveform is proportional to the intensity of the magnetic field. (In actuality, a delay occurs because of the inductance component of the driving coil 1).

When the driving coil 1 thus applies a magnetic field variation to the nugget A, a magnetic after-effect is generated due to the peculiar nature of each substance involved; and since martensite is formed in the nugget A as a result of rapid cooling after the spot welding. A difference occurs between the magnetic after-effect generated in the nugget A and the magnetic after-effect generated in the areas outside the nugget A. More specifically, the following relationship occurs:

Relaxation time constant of nugget A>Relaxation time constant of areas outside nugget A.

Figure 3:
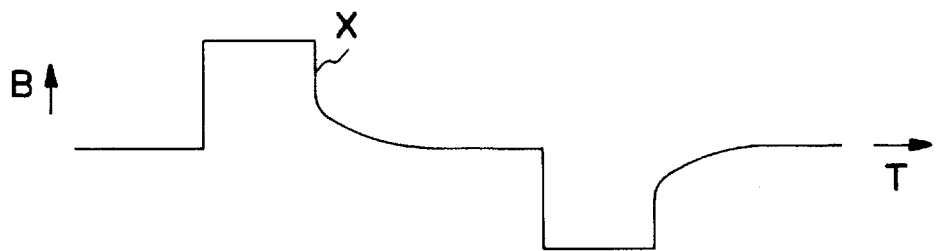
FIG. 3 shows the pulse waveform obtained in the spot welded nugget.
Figure 4:
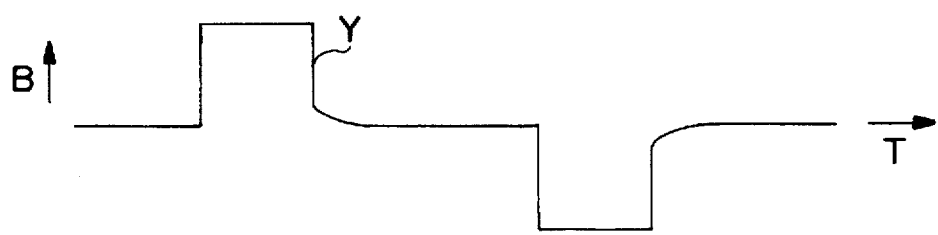
FIG. 4 shows the pulse waveform obtained in areas outside the spot welded nugget.

Accordingly, a waveform X such as that shown in FIG. 3 is obtained in the nugget A, while a waveform Y such as that shown in FIG. 4 is obtained in the areas outside the nugget A.

By pulse-driving the driving coil 1, it is possible to make the magnetic after-effect more conspicuous; and by driving the driving coil 1 in the positive and negative directions, it is possible to prevent the magnetization of the nugget A which is spot welded and measured.

This magnetic after-effect is detected by the magnetism sensing element 3 that is set to face the nugget A, and a data processing is performed in the control section 4, thus measuring the welding conditions of the nugget A.

FIG. 5 illustrates a plurality of magnetism sensing elements 3 which are disposed in an array arrangement having the form of a checkerboard. With this structure, magnetic after-effect data can be obtained for a broader area including the nugget A and its surroundings, so that the welding conditions and shape of the nugget A can be measured more clearly and in much greater detail, thus being extremely effective.

If, as shown in FIG. 5, 16 magnetism sensing elements 3 are installed in an array form so as to face a specific area including the nugget A and the area around the nugget A, and the driving coil 1 is pulse-driven, then variations in magnetic flux density appear in the respective magnetism sensing elements 3 in accordance with the properties of the facing portions of the object to be measured.

Accordingly, if the magnetism sensing elements 3 installed in the array are grouped together in groups of four each as shown in FIG. 6 so as to simplify the processing of the signals from the magnetism sensing elements 3, and if the four + side outputs and four − side outputs of the four respective magnetism sensing elements 3 of each group are switched at high speed by respective analog, S/W's 8 so that these outputs are converted into one + side output and one − side output which are differentially amplified, then four signals, each consisting of the superimposed signals of four magnetism sensing elements 3, are obtained. These signals are separated and analyzed after performing A/D conversion, so that the shape and welding conditions of the nugget A are measured and displayed based upon the physical properties of the various portions which are located inside the prescribed area including the nugget A and its surroundings which face the 16 magnetism sensing elements 3.

The present invention is constructed as described above, and it measures the welding conditions and shape of a spot welded nugget A by utilizing the magnetic after-effect that is generated when a magnetic field variation is applied to the nugget A. Accordingly, all nuggets can be detected in a non-destructive manner with no need to use extra material such as samples, etc., and such detections can be performed off-line with internal defects occurring immediately after welding being also detected. Moreover, the welding conditions and shapes of the nuggets can be measured easily and accurately without any danger of error occurring in individual measurements. Accordingly, the apparatus of the present invention is extremely convenient.

We claim:

1. An apparatus for detecting a nugget for spot welding, said apparatus comprising a driving coil which applies a pulsed alternating positive and negative magnetic field to a spot welded nugget and a magnetism sensing element provided between said driving coil and said spot welded nugget, said magnetism sensing element for detecting, between an occurrence of positive and negative magnetic field pulses, variations in magnetic flux density arising in the vicinity of said nugget as a result of said pulsed alternating positive and negative magnetic field.

2. An apparatus for detecting a nugget for spot welding according to claim 1, wherein said magnetism sensing element comprises a plurality of magnetic sensing elements disposed in an array so as to face said nugget and an area around said nugget.

* * * * *